US012779449B2

(12) United States Patent
Olivier

(10) Patent No.: US 12,779,449 B2
(45) Date of Patent: Nov. 3, 2026

(54) TRANSFER MECHANISM FOR TRANSFERRING OBJECTS THROUGH A TRANSFER PORT

(71) Applicant: Merck Patent GmbH, Darmstadt (DE)

(72) Inventor: Stephane Olivier, Molsheim (FR)

(73) Assignee: Merck Patent GmbH, Darmstadt (DE)

( * ) Notice: Subject to any disclaimer, the term of this patent is extended or adjusted under 35 U.S.C. 154(b) by 720 days.

(21) Appl. No.: 18/032,878

(22) PCT Filed: Oct. 20, 2021

(86) PCT No.: PCT/EP2021/079026
§ 371 (c)(1),
(2) Date: Apr. 20, 2023

(87) PCT Pub. No.: WO2022/084367
PCT Pub. Date: Apr. 28, 2022

(65) Prior Publication Data

US 2023/0390756 A1 Dec. 7, 2023

(30) Foreign Application Priority Data

Oct. 23, 2020 (EP) .................................... 20306270

(51) Int. Cl.

| | |
|---|---|
| ***B01L 1/02*** | (2006.01) |
| ***A61L 2/26*** | (2006.01) |
| ***B01L 1/04*** | (2006.01) |
| ***B01L 9/00*** | (2006.01) |
| ***B25J 21/00*** | (2006.01) |

(Continued)

(52) U.S. Cl.
CPC ................. *B01L 1/025* (2013.01); *A61L 2/26* (2013.01); *B01L 1/04* (2013.01); *B01L 9/52* (2013.01); *C12M 23/48* (2013.01); *C12M 23/52* (2013.01); *C12M 37/00* (2013.01); *B01L 2200/025* (2013.01); *B01L 2200/141* (2013.01);

(Continued)

(58) Field of Classification Search
None
See application file for complete search history.

(56) References Cited

U.S. PATENT DOCUMENTS

| | | | |
|---|---|---|---|
| 5,783,156 | A | 7/1998 | Renzi et al. |
| 2003/0155846 | A1 | 8/2003 | Sacca |

(Continued)

FOREIGN PATENT DOCUMENTS

| | | | |
|---|---|---|---|
| EP | 0730907 | A2 | 9/1996 |
| GB | 2237816 | A | 5/1991 |

(Continued)

OTHER PUBLICATIONS

International search report PCT/EP2021/079026 dated Jan. 24, 2022 (pp. 1-3).

*Primary Examiner* — Holly Kipouros
(74) *Attorney, Agent, or Firm* — Millen, White, Zelano & Branigan P.C.; William F. Nixon

(57) ABSTRACT

Transfer mechanism/device (40) transferring one or more objects (O) through a transfer port (R), having a supporting base (41), a shuttle (42) with a mount (43) for a holder (47) for the one or more objects (O) or with a holder (47) and a container (44) accommodating the base (41) and the shuttle (42) and accommodating the objects (O), and having at least one opening (45) at an end portion in an axial direction (X) of the container (44).

18 Claims, 8 Drawing Sheets

(51) Int. Cl.
*C12M 1/00* (2006.01)
*C12M 1/12* (2006.01)
*C12M 3/00* (2006.01)

(52) U.S. Cl.
CPC .................. *B01L 2300/0609* (2013.01); *B01L 2300/0832* (2013.01)

(56) References Cited

U.S. PATENT DOCUMENTS

| | | | | |
|---|---|---|---|---|
| 2017/0247132 | A1* | 8/2017 | Deutschle | B01L 1/02 |
| 2018/0362910 | A1* | 12/2018 | Bores | C12M 23/38 |
| 2022/0055232 | A1 | 2/2022 | Gabusi | |

FOREIGN PATENT DOCUMENTS

| | | | |
|---|---|---|---|
| WO | 2017129362 | A2 | 8/2017 |
| WO | 2020144722 | A1 | 7/2020 |

* cited by examiner

TRANSFER MECHANISM FOR TRANSFERRING OBJECTS THROUGH A TRANSFER PORT

TECHNICAL FIELD

The present application relates to a transfer mechanism or device for transferring one or more objects through a transfer port into or from a clean processing area. The present application particularly concerns the field of testing in pharmaceutical and food processing and more particularly environmental monitoring of clean or ultra clean processing areas. It is also applicable to other processing situations where cleanness of a processing area or environment is to be determined and monitored, for example in the field of semiconductor, electronics or aircraft manufacturing.

BACKGROUND

In order to monitor environmental conditions in closed processing areas of the above type it is common practice in passive air sampling to place one or more media plate/plates in an activity zone of the clean production area or isolator (both terms will be used interchangeably in this specification) and expose them to the surrounding air such that they can capture the maximum amount of particles in the surrounding air. Larger particles tend to settle faster on the plates due to gravitational force. Smaller particles take some time in settling due to factors such as air currents. Media plates work best in still areas. The microorganisms from the air may settle on the media plates alone or in colonies.

In active monitoring of air in production areas a microbial air sampler is used to force air into or onto a collection medium over a specified period of time. The collection medium can be a common petri-dish, for example including a nutrient agar-based test media or other suitable test media depending on the need.

The collection media, for example in the form of the media plates, petri-dishes or settle plates (the terms will be used interchangeably in this specification), have to be transferred repeatedly into the production area and removed therefrom for further handling and evaluation. This is commonly done in a manual process where one or more plates or petri-dishes are conveyed manually through a sterile transfer port into and from the interior of the production area. However, the manual handling of the petri-dishes involves a high risk of contamination when handling the media plates, i.e. that lids are inadvertently opened, displaced or removed from their media plates during handling involving introduction, installation and removal, thereby compromising the detection result, in particular when a plurality of them are handled in a set, a stack or in batches.

Sterile transfer ports for selective access through a valve to a clean processing area without compromising the sterility are known. Such systems are also known as "RIP" or "rapid transfer ports" and the invention is directed to a transfer mechanism or device that is useful in conjunction with such a transfer port, i.e. is configured so as to be compatible with the respective valve design of the transfer port but can be universally applied to existing designs.

For example, GB 2237816 A1 discloses a double-door transfer port which allows a contained transfer between a container and an isolator, i.e. a clean processing area. The container is docked with its closed port and then, from within an isolator, the port door is opened. The docking of the container to the transfer port of the isolator may be accomplished using a bayonet system by twisting the container around its axis to dock it into place at the port. Because the container must be physically rotated, the contents thereof are also subjected to rotation, which may spill liquids or damage delicate equipment. In this prior art, the whole of the lid and bayonet-closure mechanism of the container are housed in a short cube- or -collar-like extension of the container mounted on the container itself via a gas-tight slip-ring joint. With such an arrangement, the extension is rotated to dock the container into place onto the port, but because of the slip-ring joint, the container need not rotate. This device only presents the open container to be accessible from the inside of the isolator, thus making the handling of the objects difficult, in particular where the objects to be transferred are media plates, petri-dishes or settle plates for the reasons given above.

The present application considers application of the transfer principle of docking a container which holds one or more objects to be transferred to a rapid transfer port of an isolator, opening the port and transferring the objects from the container into the isolator and vice versa.

The present application aims at providing a transfer mechanism or device for transferring one or more objects, in particular petri-dishes as the objects to be transferred, through the transfer port in an active process without compromising the sterility.

SUMMARY

To solve the problem, the present application provides a transfer mechanism or device for transferring one or more objects through a transfer port, in particular petri-dishes, with the features of claim 1. Preferred embodiments are defined in the dependent claims.

The present application specifically provides a transfer mechanism/device for transferring one or more objects through a transfer port, comprising a supporting base, a shuttle with a mount for attaching a holding means for the one or more objects or with a holding means for the one or more objects, and a container accommodating the supporting base and the shuttle and configured to accommodate the one or more objects, and having at least one opening at an end portion in an axial direction of the container. The shuttle is arranged at the supporting base for a translational motion along the axial direction and is configured to thereby move the holding means with the one or more objects, and the container is configured to be coupled to the transfer port to allow the one or more objects to be moved into or out from the container through the at least one opening in that the shuttle translates in the axial direction.

Preferably, the mount comprises a connector for releasably connecting/attaching the holding means for the one or more objects with the mount.

Preferably, the shuttle is guided at and along the supporting base and/or the container for the translational motion by complementary guiding means on the shuttle and the supporting base and/or the container.

Preferably, the mount or the holding means is articulated with the shuttle to allow a pivoting motion of the mount or holding means relative to the shuttle about at least one rotation axis.

Preferably, the mount or holding means is articulated with the shuttle to allow the pivoting motion of the mount or holding means about the at least one rotation axis at a defined axial position of the translational motion.

Preferably, the pivoting range of the mount or holding means is configured to allow a change of posture of the objects by about 90°, preferably from an essentially horizontal orientation to an essentially vertical orientation or vice versa.

Preferably, the at least one rotation axis is arranged such that the pivoting motion of the mount/holding means is aided by gravity at the defined axial position of the translational motion.

Preferably, the transfer mechanism further includes a transfer actuator accessible from the outside of the container and configured to effect the translational motion of the shuttle along the axial direction.

Preferably, the transfer actuator includes a first rod connected with the shuttle to effect the translational motion.

Preferably, the transfer actuator includes a second rod articulated with the mount/holding means to effect the pivoting motion relative to the shuttle.

Preferably, the transfer mechanism further includes a first stopper defining an end position of the pivoting motion and/or a second stopper defining an end position of the translational motion.

Preferably, the end position of the translational motion is coincident with the defined axial position where the pivoting motion of the mount or holding means relative to the shuttle about the at least one rotation axis is possible.

Preferably, the shuttle is configured to be pulled/pushed from the side of the opening to effect the translational motion and/or the pivoting motion, if provided.

Preferably, the holding means is one that is configured to hold a plurality of Petri-dishes in an aligned parallel orientation.

Preferably, the transfer mechanism further comprises a door configured to selectively close the at least one opening of the container, wherein the door is preferably configured to be connectable to the transfer port, preferably a transfer port in an "alpha part door design".

The present application also provides for a process for transferring one or more objects through a transfer port into a sterile or at least clean processing area or isolator, the process comprising the steps of (a) providing a transfer mechanism/device as defined in the present application and comprising one or more objects, said one or more objects preferably being one or more petri-dishes, held in holding means;

(b) attaching the transfer mechanism/device to the transfer port;

(c) opening the transfer port, thereby exposing the inside of the container of the transfer mechanism/device to the inside of the sterile or at least clean processing area or isolator;

(d) moving the shuttle by translational motion along its latitudinal direction into the sterile or at least clean processing area or isolator; and (e) removing one or more of objects from the holding means.

Preferably, step (d) of the process comprises the following steps (d') moving the shuttle by translational motion along its latitudinal direction into the sterile or at least clean processing area or isolator to a defined axial position of the translational motion; and (d") pivoting the mount or the holding means about the at least one rotation axis at the defined axial position of the translational motion, optionally simultaneously continuing moving the shuttle by translational motion along its latitudinal direction to an end position of the translational motion.

Preferably, in step (d") the mount or holding means is pivoted by essentially 90°, thereby preferably bringing the one or more objects (O) from an essentially vertical orientation to an essentially horizontal orientation or vice versa.

BRIEF DESCRIPTION OF THE DRAWINGS

In the following various embodiments will be described by reference to the attached exemplary schematic drawings, in which.

DETAILED DESCRIPTION

Figure 1:
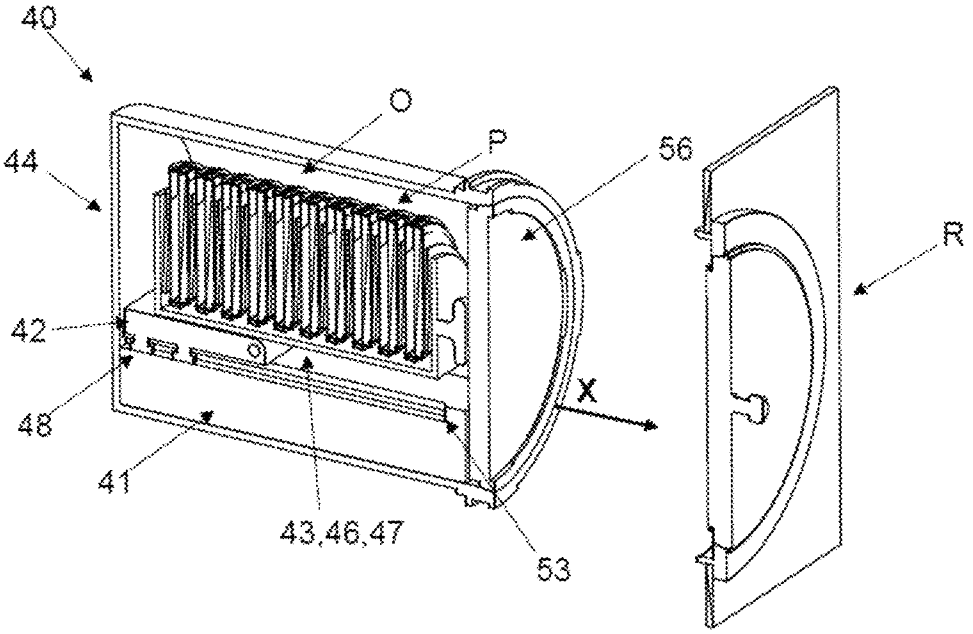
FIG. 1 is a partially cut-away perspective side view of a transfer mechanism/device of an embodiment prior to docking the mechanism to a transfer port.

For the purposes of the present application, terms such as "horizontal", "vertical", "perpendicular", and similar terms are—if not already explicitly indicated—considered to be "essentially horizontal", "essentially vertical", "essentially perpendicular", provided that this does not negatively affect functionality. Preferably, the term "essentially" is to denote a deviation of at most 10°, more preferably of at most 5°, even more preferably of at most 4° or 3°, still even more preferably of at most 2° or 1° from being horizontal, vertical, and perpendicular, respectively.

The present invention accordingly provides a solution for aseptically transferring one or more objects, preferably petri-dishes, through a rapid transfer port in a controlled standardized process that is compatible with environmental monitoring in a fully automated process in a sterile environment.

The transfer mechanism is compatible with the existing standard rapid transfer ports for an isolator and petri-dishes or settling plates and is capable of presenting the petri-dishes in an essentially horizontal orientation, preferably with the lid on top, in a convenient and repeatable way for manual or automated gripping, for example by a robot grip. Thereby, transfer into and out from the isolator can be performed in an easy, controlled and reliable manner.

Further, there is no risk of unintentional opening or dislodging of lids of petri-dishes during the transport into the isolator or from the isolator due to the defined translational motion performed by the shuttle holding the petri-dishes.

The design with the shuttle provides for a compact structure and a low footprint inside the isolator needed to present the objects (i.e. petri-dishes) for further handling.

Further, the petri-dishes are presented in a defined position, thereby facilitating cooperation with a gripper of an automated handling device (i.e. a robot) while still allowing a manual processing or handling if needed.

In the following various embodiments of a process of transferring one or more objects into or out from an isolator or clean production area using the transfer mechanism of the present application will be described.

The embodiment of the transfer mechanism/device 40 for transferring one or more objects O, preferably petri-dishes, to a transfer port R comprises, as its basic components, a supporting base 41 and a shuttle or slide 42 that is arranged at the supporting base 41 for a translational motion along a longitudinal direction X. The shuttle 42 is provided with a mount 43 or nest configured to hold, in a releasable manner, a holding means 47 for the one or more objects O or it is already provided with such a holding means 47 for the one or more objects to be transferred.

The transfer mechanism 40 further comprises a container 44 which accommodates the supporting base 41 and the shuttle 42 and which is configured to accommodate the one or more objects O on the holding means 47. The container 44 has at least one opening 45 at an end portion in an axial direction of the container which corresponds to the longitudinal direction X of the translational motion.

The translational motion of the shuttle 42 along the longitudinal/axial direction X allows movement of the holding means 47 with the objects back and forth towards or from the opening 45 of the container 44.

The container 44 is configured to be coupled or docked to the rapid transfer port R in a releasable manner by suitable engagement features designed according to the respective coupling concept of the transfer port. After docking the transfer port with a lid of the container to be described later is opened so as to expose the inside of the container to the inside of the isolator and so as to allow the one or more objects to be moved into or out from the container 44 through the at least one opening 45 in that the shuttle 42 translates in the axial direction.

The various stages of operation of the transfer mechanism or more precisely the docking of the container to the transfer port, the translation of the shuttle with the objects out from the opening 45 and the presentation of the objects inside the isolator are explained on the basis of the sequence of FIGS. 1 to 3, 5 and 6.

The shuttle 43 is slidably guided at and along the supporting base 41 and/or the container 44, for example its inner walls for the translational motion by complementary guiding means 48 on the shuttle 42 and the supporting base 41 and/or the container 44. The guiding means 48 can be in the form of rails or grooves cooperating with complementary engagement elements.

Figure 2:
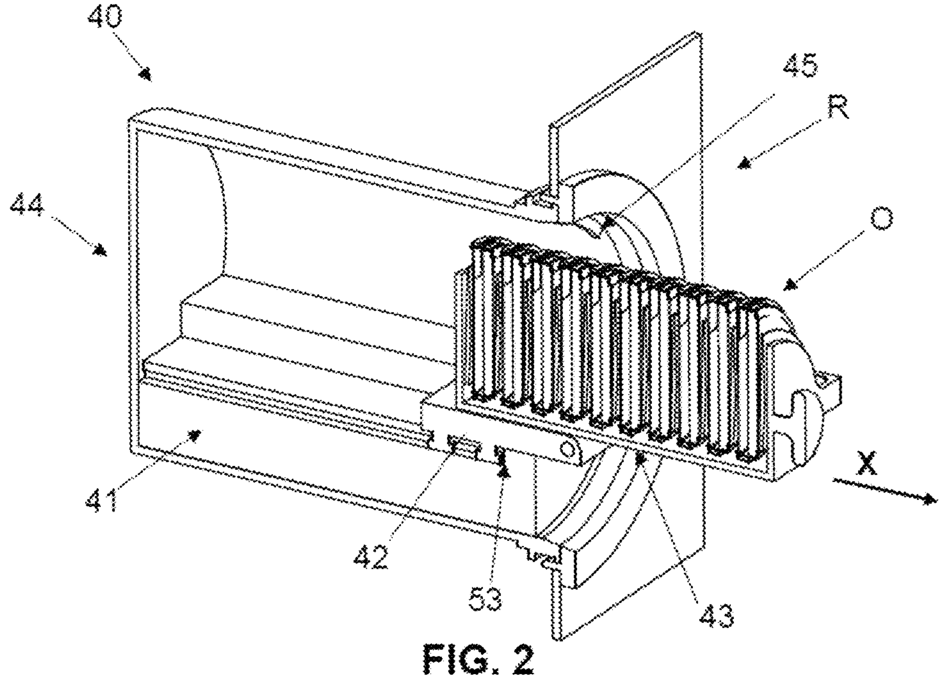
FIG. 2 is a partially cut-away view similar to that of FIG. 1 of the transfer mechanism of the embodiment after docking to the transfer port and opening.
Figure 3:
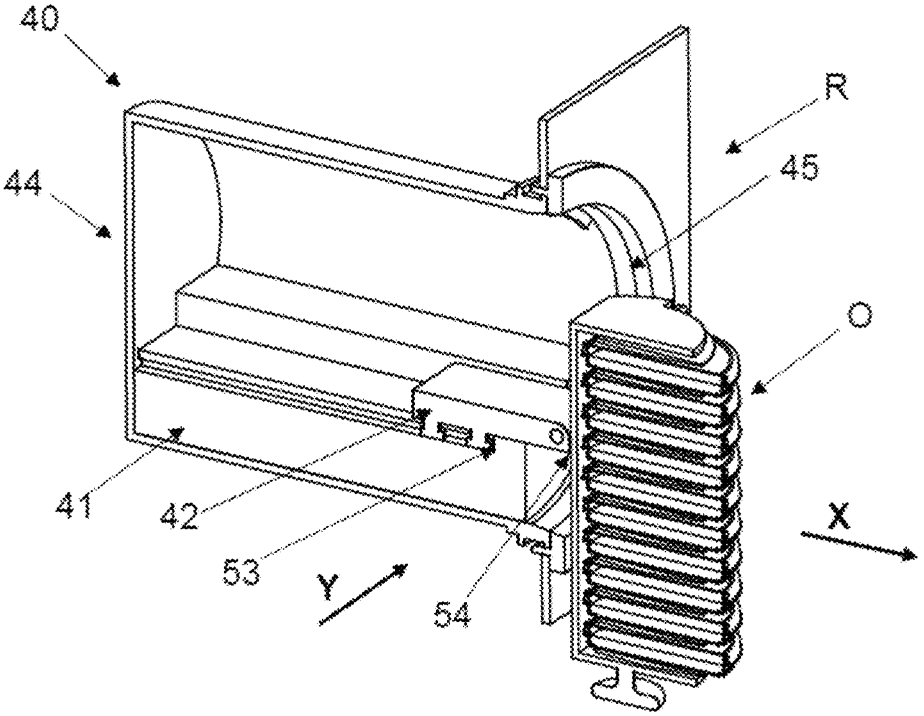
FIG. 3 is a partially cut-away view of the transfer mechanism of FIGS. 1 and 2 with the holding means arranged in a pivoted end position outside the container.
Figure 4:
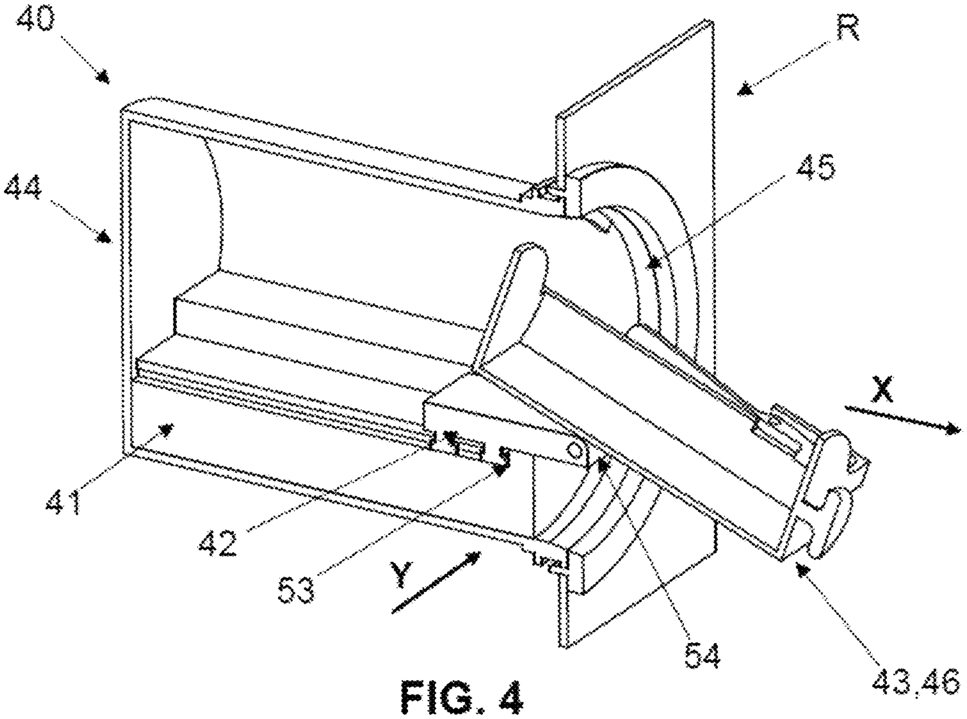
FIG. 4 is a partially cut-away view of the transfer mechanism of the embodiment with the holding means empty in the process of transfer out from the container.

The transfer mechanism includes a first stopper 53 defining an end position of the translational motion towards the opening 45 at the end portion in the axial direction of the container (see FIGS. 2 to 4). The transfer mechanism may further comprise a stopper defining the end position of the translational motion into the container on an opposite end portion in the axial direction.

The supporting base 41 may be formed as a separate element from the container and arranged inside its interior or may be an integral part of the container. The mount 43 for removably connecting to a holding means 47 for the objects or the holding means 47 (in a case where the holding means is connected with the slide of the transfer mechanism and is not removable therefrom, but directly holds the one or more objects) is preferably articulated with the shuttle 42 to allow a pivoting motion of the mount 43 (with the holding means) or of the holding means 47 relative to the shuttle 42 about at least one rotation axis Y which is preferably essentially perpendicular to the longitudinal direction X. The rotation axis Y in the form of a hinge or joint is provided on a forward end of the shuttle 42 as shown, for example, in FIG. 4.

Preferably, the mount 43 (or the holding means 47) is articulated with the shuttle 42 to allow the pivoting motion of the mount/holding means about the at least one rotation axis Y at a defined axial position during the translational motion, preferably at the end position at the end portion of the opening 45 of the container 44 as shown in FIGS. 3 and 4. Depending on the form and dimension of the mount 43/holding means 47, the pivoting motion can commence a certain distance before the end position is reached but is prevented during the translational motion before a certain point is reached.

The pivoting range of the mount 43/holding means 47 is configured to allow a change of posture of the objects by about 90 degrees, preferably from an essentially vertical orientation to an essentially horizontal orientation (as shown in FIGS. 1 to 3) or vice versa. Smaller or larger pivoting ranges are possible depending on the situation.

The at least one rotation axis Y is arranged such that the pivoting motion of the mount 43/holding means 47 is at least aided by gravity at the defined axial position of the translational motion. Preferably, the pivoting motion is initiated and fully performed by gravity at a certain point so that no further external introduction of force is required. Moving back the shuttle into the container may, due to an interaction between the mount/holding means with portions of the container force the mount/holding means to pivot back around the rotation axis Y into an essentially horizontal state for further unhindered translational movement into the container.

Figure 5:
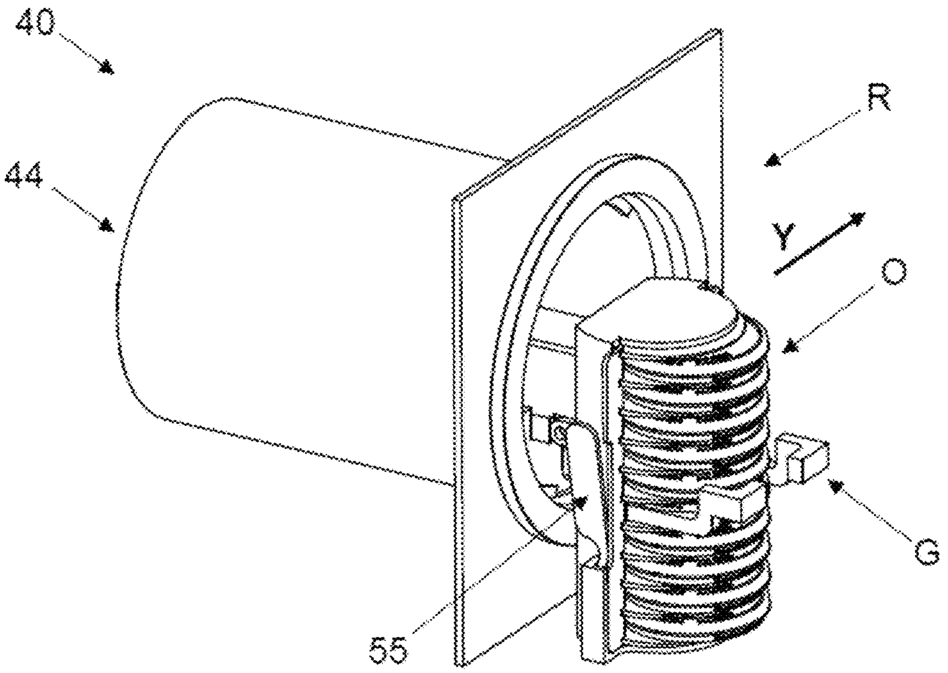
FIG. 5 is a perspective view of the transfer mechanism of the embodiment similar to the one of FIG. 3 showing schematically the gripper of an automated handling device engaging with one of the petri dishes.

The mount 43 preferably comprises a connector 55 for releasably connecting the holding means 47 for the objects to the mount 43 (see FIG. 5). The holding means 47 in this case can be in the form of a rack with a plurality of receptacles for securely holding the objects separated from each other (preferably petri-dishes) in an aligned orientation. As described above, the holding means can be integrated into the transfer mechanism, so that the objects can be directly loaded into the transfer mechanism. The releasable connection via the connector 55 provides the advantage, however, that the objects can be prepared in the holding means and quickly loaded into the transfer mechanism.

Figure 6:
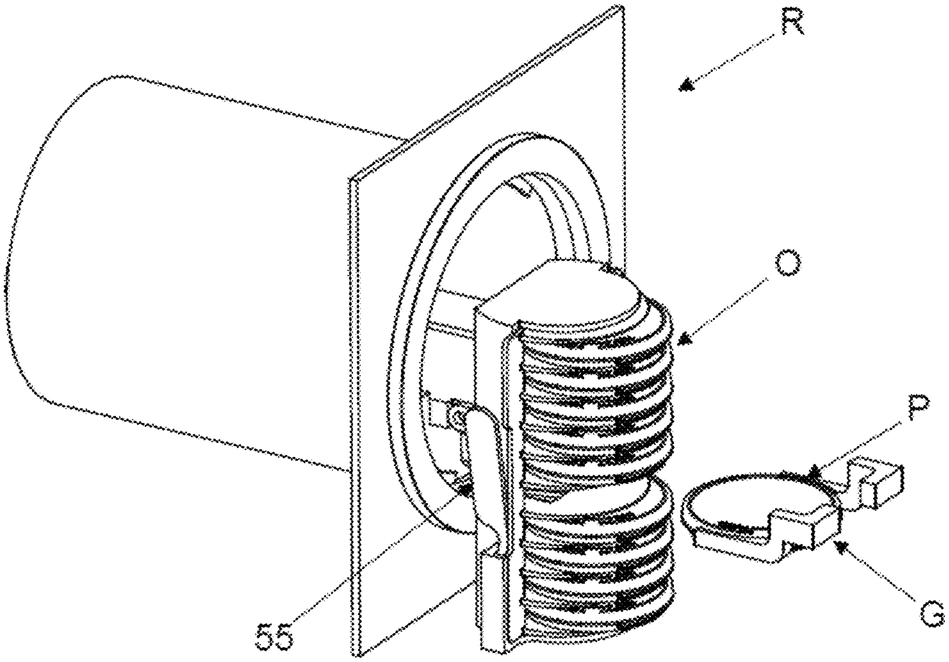
FIG. 6 is a partial perspective view similar to the one of FIG. 5 with the petri-dish removed by means of the gripper of the automatic handling device.
Figure 7:
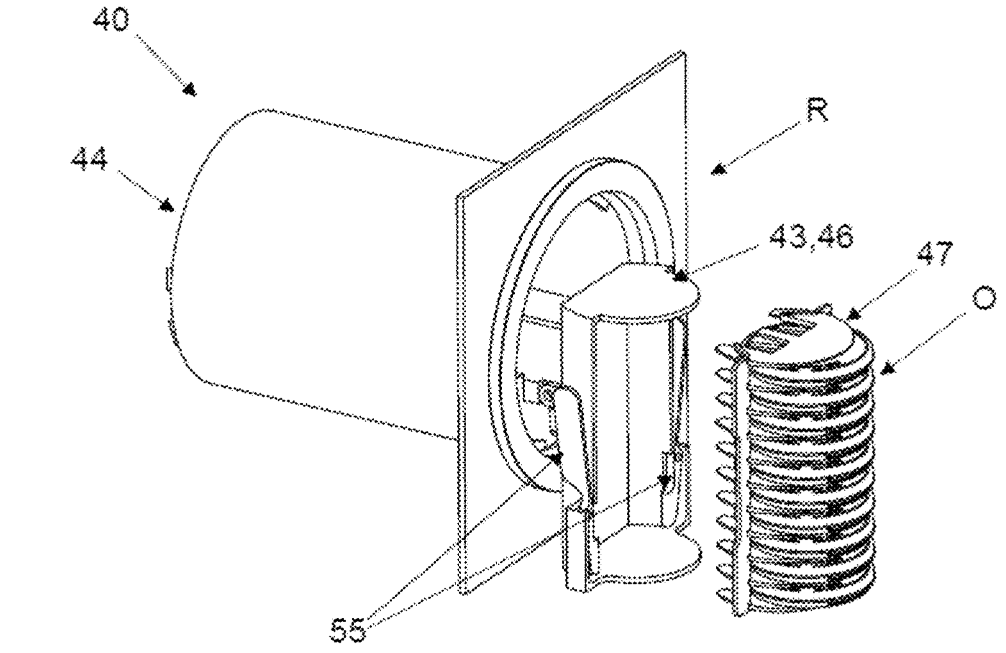
FIG. 7 is a perspective view of the present transfer mechanism similar to the one of FIG. 5 with the holding means in the form of a rack removed from the holding means.

When fully transferred out from the inside of the container through the opening of the container into an isolator (after the door of the transfer port together with the lid of the container has been opened), each object (petri-dish) is easily accessible in the inside of the isolator and can be grabbed and taken out from the holding means by hand or by means of a lateral gripper G of a robot (see FIGS. 5 and 6). Depending on the dimension of the holding means the rotational axis Y is arranged at a position of about one third of the overall length to minimize the displacement necessary to bring the holding means out from the opening and to minimize the intrusion to the inside of the isolator. Other positions are possible depending on the dimensions. Further, depending on the location of the rotation or pivot axis the pivoting of the holding means may be prevented until it is completely transferred inside the isolator.

The end position of the translational motion is preferably coincident with the defined axial position where the pivoting motion of the mount 43/holding means 47 relative to the shuttle 42 about the at least one rotation axis Y is possible.

The shuttle 42 is configured to be pulled/pushed from the side of the opening 45 to effect the translational motion and/or the pivoting motion, if provided. The pulling/pushing force may be provided by an automated handling device, for example via the gripper. In some cases it may be impossible to actuate the travelling mechanism for translation and rotation from the inside of the isolator.

Figure 8:
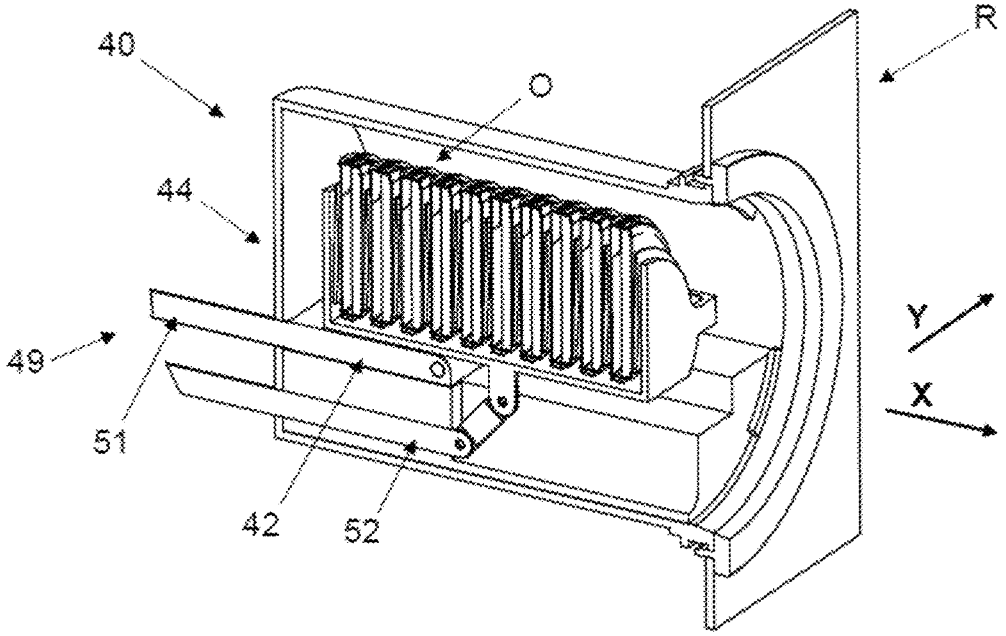
FIG. 8 is a partially cut-away view of the present transfer mechanism similar to the one of FIG. 2 according to a modified embodiment.
Figure 9:
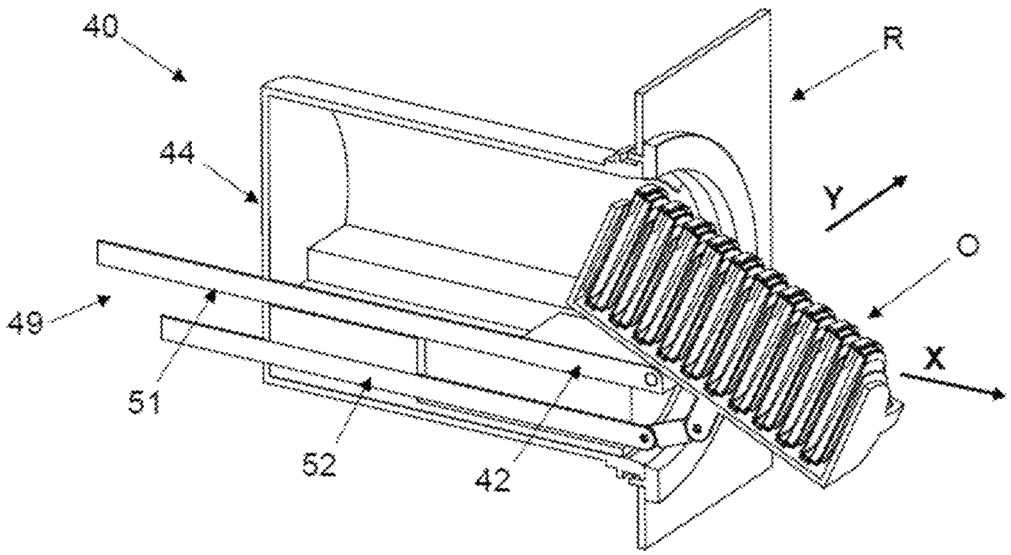
FIG. 9 is a partially cut-away view of the modified embodiment of FIG. 2 in a translational position similar to the one of FIG. 4.
Figure 10:
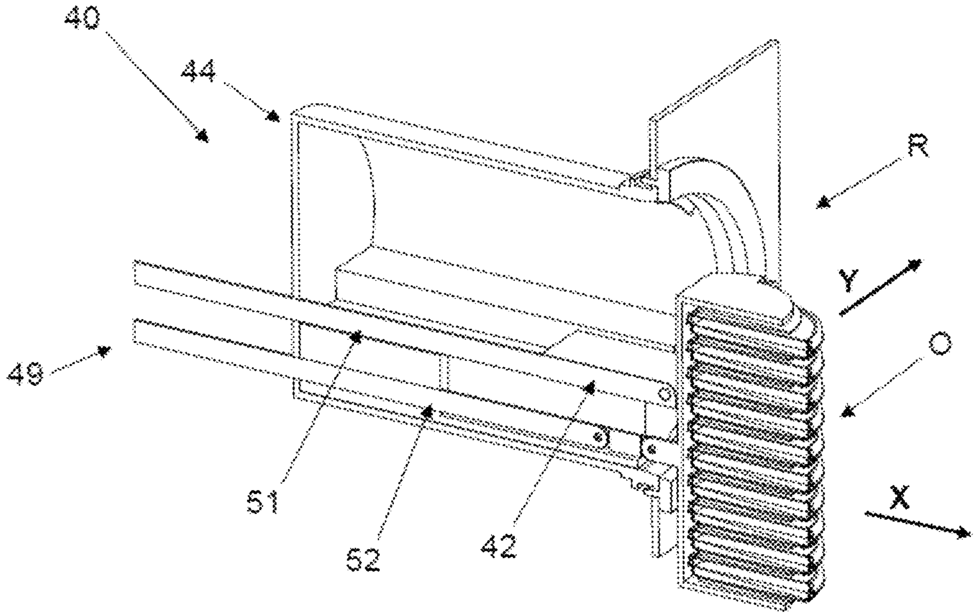
FIG. 10 is a partially cut-away view of the modified embodiment in a transfer position similar to the one of FIG. 3.

According to the modification of the preferred embodiment shown in FIGS. 8 to 10 a transfer actuator 49 may be provided in the transfer mechanism which is accessible from the outside of the container 44 and which is configured to effect the translational motion of the shuttle 42 along the axial direction X. The transfer actuator 49 of the modified embodiment may include a first rod 51 connected to the shuttle 42 to effect the translational motion. Further, the transfer actuator 49 may include a second rod 52 articulated with the mount 43/holding means 47 to initiate and effect the pivoting motion relative to the shuttle 42 around the rotation axis Y. The kinematics of the transfer actuator 49 may be operated by hand or by a mechanic actuator like a hydraulic cylinder, a servo motor or a linear drive. The rods leading out from the container are sealed relative to the inside of the container so as to maintain the sterility of the inside of the container during operation. The rods may also be integrated in a part of the base 41, so as to be sealed from the inside of the container accommodating the one or more objects to be transferred. If the actuator is integrated in the container the sealing is simplified because only a power connector would be sufficient to be led to the outside.

The transfer mechanism for moving the shuttle for the translational motion and the pivoting motion is reversible to allow reloading of the objects from the inside of the isolator into the inside of the container.

The transfer mechanism, more specifically the container, may comprise a lid or door 56 configured to selectively close the at least one opening 45 of the container 44, and the door 56 is preferably configured to be connectable to the respective transfer port according to the valve concept, preferably a rapid transfer port in an alpha part door design.

The present application also relates to a process for transferring one or more objects through a transfer port R into a sterile or at least clean processing area or isolator, comprising the following steps (1) to (5) in sequence, wherein (1) a transfer mechanism/device 40 as defined in the present application and comprising one or more objects O, said one or more objects O preferably being one or more petri-dishes P, held in holding means 47, is provided; (2) the transfer mechanism/device 40 is attached to the transfer port R; (3) the transfer port R is opened, thereby exposing the inside of the container 44 of the transfer mechanism/device 40 to the inside of the sterile or at least clean processing area or isolator; (4) the shuttle 42 is moved by translational motion along its latitudinal direction (X) into the sterile or at least clean processing area or isolator; and (5) one or more of objects O is removed from the holding means 47 and may be used as intended inside the sterile or at least clean processing area or isolator, for example, in monitoring environmental conditions, for example, in air sampling.

Preferably shuttle 42 is moved by translational motion along its longitudinal direction X into the sterile or at least clean processing area or isolator to a defined axial position of the translational motion (expressed differently, until a defined position along the longitudinal direction X has been reached); and then pivoting the mount 43 or the holding means 47 about the at least one rotation axis Y at the defined axial position of the translational motion, possibly/optionally simultaneously continuing moving the shuttle 42 by translational motion along its latitudinal direction X to an end position of the translational motion.

Said translational motion of the shuttle 42 may be done directly to the end position, followed by the pivotal motion of the mount 43 or the holding means 47. Alternatively, the defined axial position of the translational motion of the shuttle 42 may be located before the end position of said translational motion is reached, i.e. before the shuttle 42 has reached the final position for unloading, in which case said translational motion may be continued to the end position while simultaneously pivoting the mount 43 or the holding means 47.

Preferably in step (d") the mount (43) or holding means (47) is pivoted by essentially 90°, thereby preferably bringing the one or more objects (O) from an essentially vertical orientation to an essentially horizontal orientation or vice versa.

The transfer mechanism/device 40 as defined herein can be preferably used in a process that is performed in an overall sterile environment for transferring a batch or set of petri-dishes into and out from various isolators for testing the air inside one of the isolators that represents a clean production environment. An example of an outline of such a process that can be largely automated is described below in connection with the FIGS. 11 to 16.

The elements of the process include a stand-alone transfer isolator U for preparing the petri-dishes for use in the process, a production isolator V representing a clean production environment that is to be tested or monitored, a transfer mechanism 40 of the present application, a batch or set of petri-dishes provided in a sterile manner in a transport packing like a blister or bag 100, and an empty transport packing or bag 13.

Figure 11:
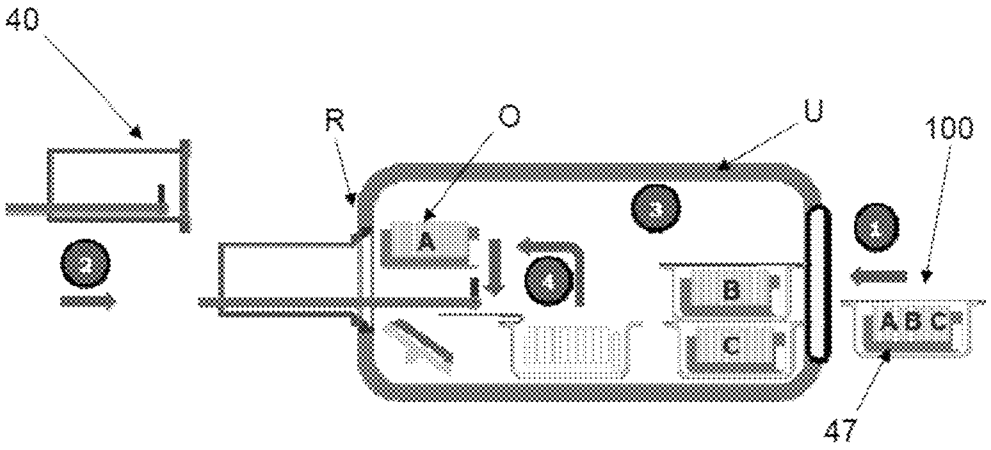
FIG. 11 is a schematic representation of the transfer process for removing objects from an isolator using the present transfer mechanism.
Figure 12:
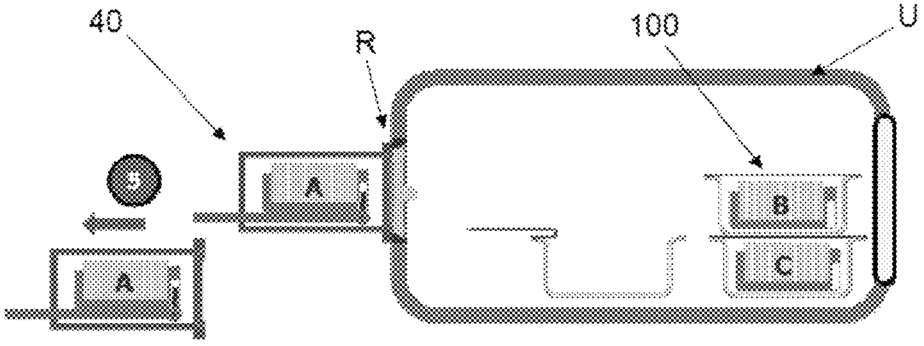
FIG. 12 is a schematic representation of the process of removing objects from the isolator using the present transfer mechanism.

As shown in FIGS. 11 and 12 several batches or sets A, B, C of sterile petri-dishes may be supplied into a transfer isolator U in the form of sealed blisters or bags 100 to maintain their sterile condition. The petri-dishes are preferably arranged in a holding means 47 (like a rack) in the respective transport packaging in order to facilitate handling of the entire batch and keeping the batch together during the process.

An empty transfer mechanism 40 as defined herein for multiple use is attached to the door of the transfer port R of the transfer isolator U, then the container door is opened by opening the transfer port.

Then, the overall environment is sterilized, if needed, including the inside of the transfer isolator and the inside of the container of the transfer mechanism.

One of the transport packagings is opened and the batch A of petri-dishes on their holding means is removed from the blister or bag and arranged inside the container of the transfer mechanism either manually or by means of an automated handling device.

Then, the door of the transfer mechanism is closed by closing the transfer port, and the transfer mechanism containing the petri-dishes in the holding means is dissociated from the isolator.

Figure 13:
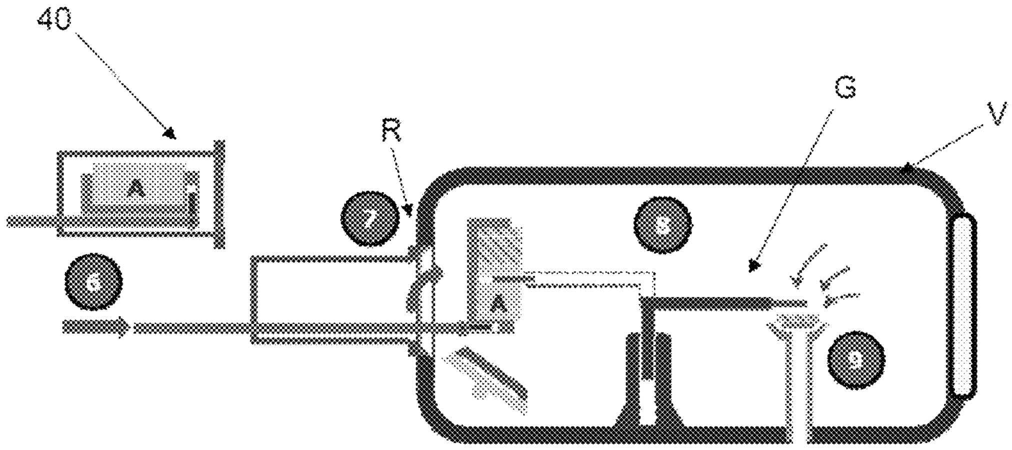
FIG. 13 is a schematic representation of the process for transferring objects into an isolator using the present transfer mechanism.
Figure 14:
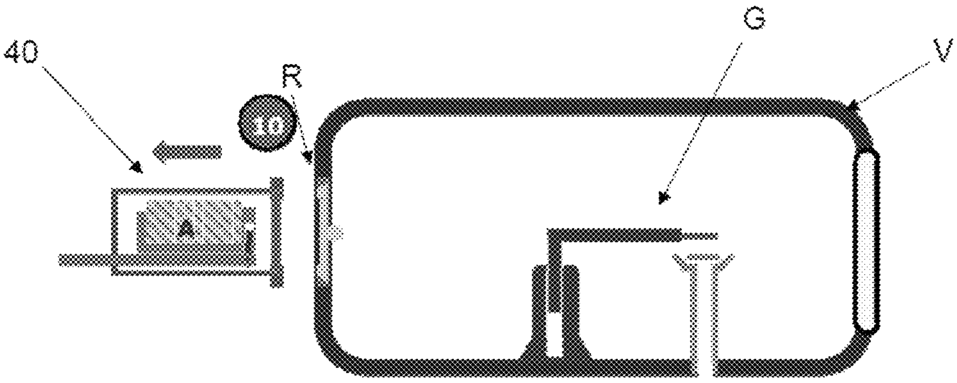
FIG. 14 is a schematic representation of the process of removing objects from an isolator using the present transfer mechanism.

Next, as shown in FIGS. 13 and 14, the transfer mechanism/device 40 is docked to the transfer port of a production isolator V, and the door is opened. By moving the shuttle in the translational direction (axial direction X), the holding means with the batch A of petri-dishes is transferred to the inside of the production isolator V and is presented to be individually grabbed by a gripper G of an automated handling device as shown in FIG. 13. The petri-dishes are processed (e.g. active or passive air monitoring as described in the introductory portion) and are put back into the holding means. Once the complete batch is processed, the holding means is retracted into the container via a shuttle of the transfer mechanism/device 40, the door of the container is closed by the transfer port R, and the transfer mechanism/device 40 is dissociated or undocked for the production isolator (see FIG. 14).

Figure 15:
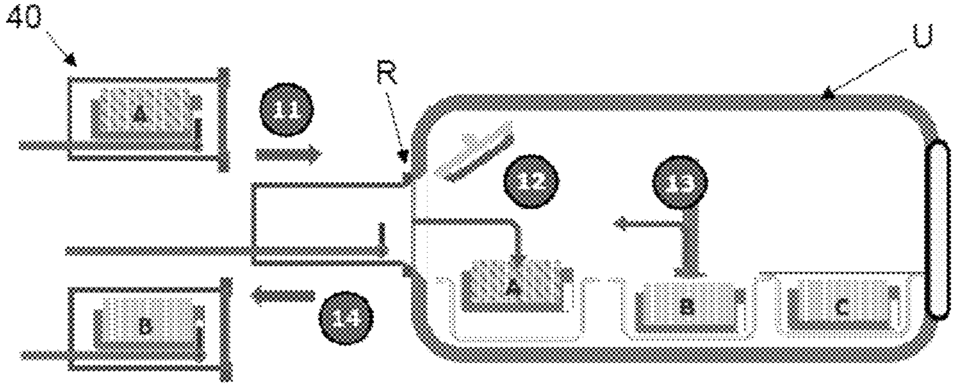
FIG. 15 is a schematic representation of the process for transferring objects into and out from the isolator using the present transfer mechanism.
Figure 16:
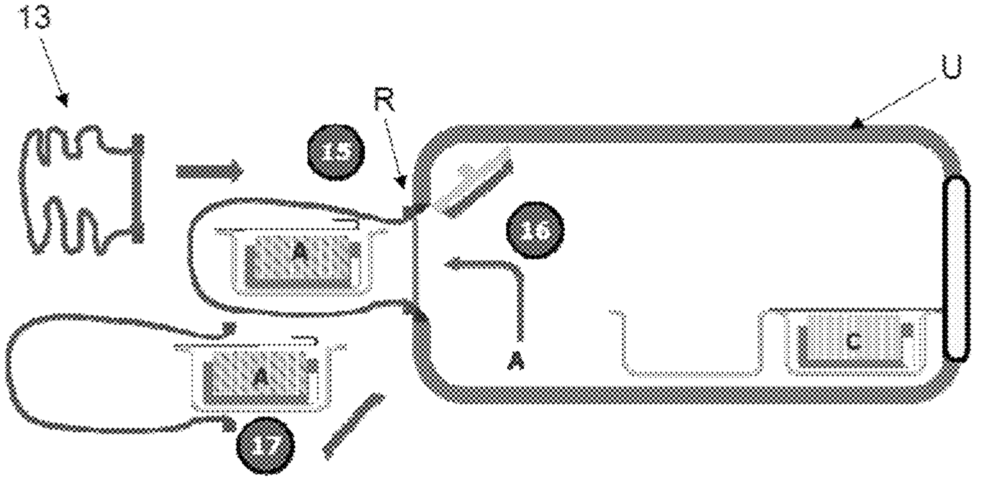
FIG. 16 is a schematic representation of the process of removing objects from an isolator using the present transfer mechanism.

In the further process shown in FIGS. 15 and 16 the transfer mechanism/device 40 with the batch A of used petri-dishes is docked again to the transfer isolator U, and the used petri-dishes on their holding device are removed from the container and placed, again, in a blister or other transport packaging. A fresh batch of petri-dishes on a holding means is transferred back into the transfer mechanism/device 40 which then is closed and undocked as in FIG. 12 (see FIG. 15).

When all the batches of petri-dishes have been used, the user can open the transfer isolator U and remove the used petri-dishes for further analysis/incubation. If desired, the analysis can be initiated without waiting until all batches have been processed. In order to remove the used petri-dishes for further processing from the transfer isolator U, the transfer mechanism/device 40 of the present application or a simple rapid transfer port bag 13 can be used and docked to the transfer port R of the transfer isolator U as shown in FIG. 16.

The invention claimed is:

1. A transfer mechanism/device (40) for transferring one or more objects (O) through a transfer port (R), comprising:
- a supporting base (41);
- a shuttle (42) with a mount (43) for attaching a holding means (47) for the one or more objects (O); and
- a container (44) accommodating the supporting base (41) and the shuttle (42) and configured to accommodate the one or more objects (O), and having at least one opening (45) at an end portion in an axial direction (X) of the container (44),
- wherein the shuttle (42) is arranged at the supporting base (41) for a translational motion along the axial direction (X) and is configured to thereby move the holding means (47) with the one or more objects (O),
- wherein the container (44) is configured to be coupled to the transfer port (R) to allow the one or more objects (O) to be moved into or out from the container (44) through the at least one opening (45) in that the shuttle (42) translates in the axial direction (X), and
- wherein the mount (43) includes a connector (55) for releasably connecting the holding means (47) for the one or more object (O) with the mount (43).

2. The transfer mechanism (40) according to claim 1, wherein the shuttle (42) is guided at and along the supporting base (41) and/or the container (44) for the translational motion by complementary guiding means (48) on the shuttle (42) and the supporting base (41) and/or the container (44).

3. The transfer mechanism according to claim 1, wherein the mount (43) is articulated with the shuttle (42) to allow a pivoting motion of the mount (43) relative to the shuttle (42) about at least one rotation axis (Y).

4. The transfer mechanism (40) according to claim 3, wherein the mount (43) is articulated with the shuttle (42) to allow the pivoting motion of the mount (43) about the at least one rotation axis (Y) at a defined axial position of the translational motion.

5. The transfer mechanism (40) according to claim 4, wherein the at least one rotation axis (Y) is arranged such that the pivoting motion of the mount (43) is aided by gravity at the defined axial position of the translational motion.

6. The transfer mechanism (40) according to claim 3, wherein a pivoting range of the mount (43) is configured to allow a change of posture of the one or more objects (O) by 90°.

7. The transfer mechanism according to claim 6, wherein the pivoting range of the mount (43) is configured to allow a change of posture of the one or more objects (O) from a horizontal orientation to a vertical orientation or vice versa.

8. The transfer mechanism (40) according to claim 1, further including a first stopper (54) defining an end position of a pivoting motion of the mount (43) relative to the shuttle (42) about at least one rotation axis (Y) and/or a second stopper (53) defining an end position of the translational motion.

9. The transfer mechanism (40) according to claim 8, wherein the end position of the translational motion is coincident with a defined axial position where the pivoting motion of the mount (43) relative to the shuttle (42) about the at least one rotation axis (Y) is possible.

10. The transfer mechanism (40) according to claim 1, further including a transfer actuator (49) accessible from the outside of the container (44) and configured to effect the translational motion of the shuttle (42) along the axial direction (X).

11. The transfer mechanism (40) according to claim 10, wherein the transfer actuator (49) includes a first rod (51) connected with the shuttle (42) to effect the translational motion.

12. The transfer mechanism (40) according to claim 11, wherein the mount (43) is articulated with the shuttle (42) to allow a pivoting motion of the mount (43) relative to the shuttle (42) about at least one rotation axis (Y), and the transfer actuator (49) includes a second rod (52) articulated with the mount (43)/holding means (47) to effect the pivoting motion relative to the shuttle (42).

13. The transfer mechanism (40) according to claim 1, wherein the shuttle (42) is configured to be pulled/pushed from a side of the at least one opening (45) to effect the translational motion and/or a pivoting motion of the mount (43) relative to the shuttle (42) about at least one rotation axis (Y), if provided.

14. The transfer mechanism (40) according to claim 1, wherein the holding means (47) is attached to the mount (43), and wherein the holding means (47) is one that is configured to hold a plurality of Petri-dishes (P) in an aligned parallel orientation.

15. The transfer mechanism (40) according to claim 1, further comprising a door (56) configured to selectively close the at least one opening (45) of the container (44).

16. A process for transferring one or more objects (O) through a transfer port (R) into a sterile or at least clean processing area or isolator, the process comprising the steps of (a) providing a transfer mechanism (40) as defined in claim 1, further comprising holding means (47) attached to the mount, and comprising one or more objects (O), held in the holding means (47);

(b) attaching the transfer mechanism (40) to the transfer port (R);

(c) opening the transfer port (R), thereby exposing the inside of the container (44) of the transfer mechanism (40) to the inside of the sterile or at least clean processing area or isolator;

(d) moving the shuttle (42) by translational motion along its latitudinal direction (X) into the sterile or at least clean processing area or isolator; and (e) removing one or more objects (O) from the holding means (47).

17. The process according to claim 16, wherein step (d) comprises the following steps (d') moving the shuttle (42) by translational motion along its latitudinal direction (X) into the sterile or at least clean processing area or isolator to a defined axial position of the translational motion; and (d") pivoting the mount (43) about at least one rotation axis (Y) at the defined axial position of the translational motion, optionally simultaneously continuing moving the shuttle (42) by translational motion along its latitudinal direction (X) to an end position of the translational motion.

18. The process according to claim 17, wherein in step (d") the mount (43) is pivoted by 90°.

* * * * *